United States Patent
de Guise et al.

(10) Patent No.: US 7,291,119 B1
(45) Date of Patent: Nov. 6, 2007

(54) SYSTEM FOR THE ANALYSIS OF 3D KINEMATIC OF THE KNEE

(75) Inventors: Jacques A. de Guise, Montréal (CA); L'Hocine Yahia, Pointe-Claire (CA); Nicolas Duval, Montréal (CA); Benoît Godbout, Montréal (CA); Annick Koller, Montréal (CA); Marwan Sati, Mississauga (CA); Nicola Hagemeister, Montréal (CA); Gérald Parent, Mascouche (CA); Ismail El Maach, Ottawa (CA)

(73) Assignees: Socovar, Société En Commandite, Montréal (CA); Polyvalor, Société En Commandite, Montréal (CA); Val-Chum, Limted Partnership, Montréal (CA)

( * ) Notice: Subject to any disclaimer, the term of this patent is extended or adjusted under 35 U.S.C. 154(b) by 216 days.

(21) Appl. No.: 10/111,922

(22) PCT Filed: Oct. 31, 2000

(86) PCT No.: PCT/CA00/01294

§ 371 (c)(1),
(2), (4) Date: Dec. 10, 2002

(87) PCT Pub. No.: WO01/32080

PCT Pub. Date: May 10, 2001

(30) Foreign Application Priority Data

Nov. 1, 1999 (CA) .................................... 2287771
Nov. 1, 1999 (CA) .................................... 2288233

(51) Int. Cl.
*A61B 5/103* (2006.01)
*A61B 5/117* (2006.01)

(52) U.S. Cl. .................................... 600/595

(58) Field of Classification Search ................ 600/595; 602/5, 16, 23, 26
See application file for complete search history.

(56) References Cited

U.S. PATENT DOCUMENTS

| 4,608,998 | A | | 9/1986 | Murdock |
| 4,804,000 | A | | 2/1989 | Lamb et al. |
| 4,911,177 | A | | 3/1990 | Lamb et al. |
| 5,586,970 | A | * | 12/1996 | Morris et al. .................. 602/26 |
| 6,050,962 | A | * | 4/2000 | Kramer et al. .............. 600/595 |
| 6,074,355 | A | * | 6/2000 | Bartlett ........................ 602/16 |
| 6,110,130 | A | * | 8/2000 | Kramer ...................... 600/595 |

FOREIGN PATENT DOCUMENTS

EP      0 710 466 A      8/1996

* cited by examiner

*Primary Examiner*—Max F. Hindenburg
*Assistant Examiner*—Jonathan Foreman
(74) *Attorney, Agent, or Firm*—Ogilvy Renault LLP

(57) ABSTRACT

A harness for attachment about a knee femur and comprised of a rigid and non-flexible frame support two resiliently mounted clamping means and sensors is described for the non-invasive measurement of knee motion and its analysis in 3-D is described. The clamping means elements are urged under pressure outwardly for application against a skin outer surface at predetermined medial and lateral sites relative to a femur. A non-resilient adjustable stabilizing element is connected to the rigid frame and disposed at a predetermined location with respect to the medial clamping element in spaced relationship therewith and adjustable for clamping contact on a skin outer surface and in alignment with the center of a medial condyle of the femur whereby to stabilize the rigid frame about a knee. An attachment rod is secured to the harness and has straps for securing the rod above the knee.

52 Claims, 6 Drawing Sheets

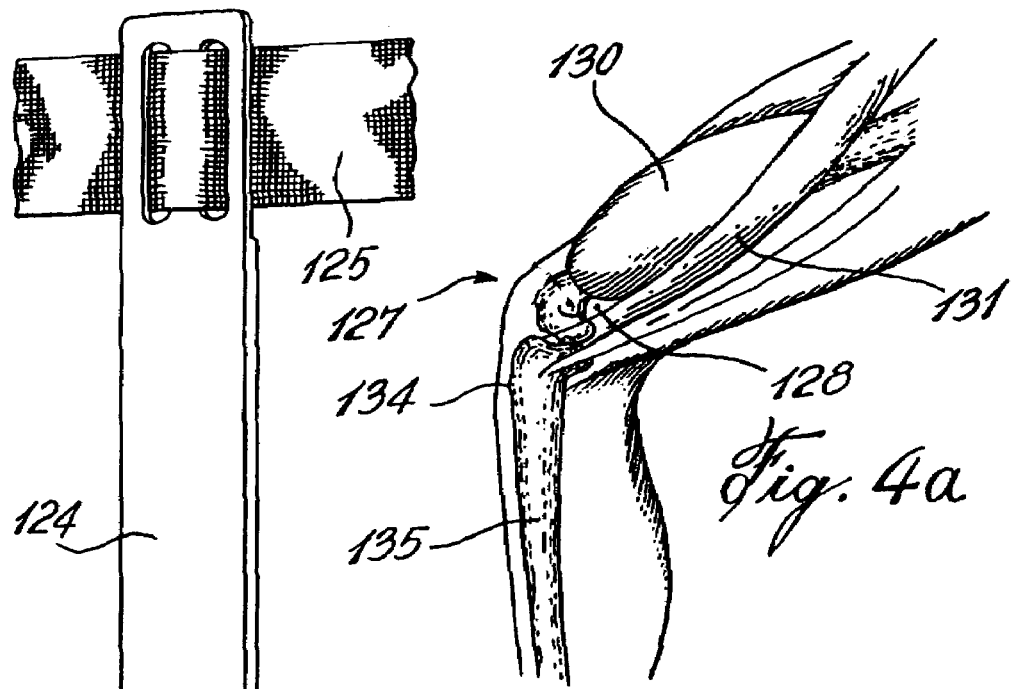
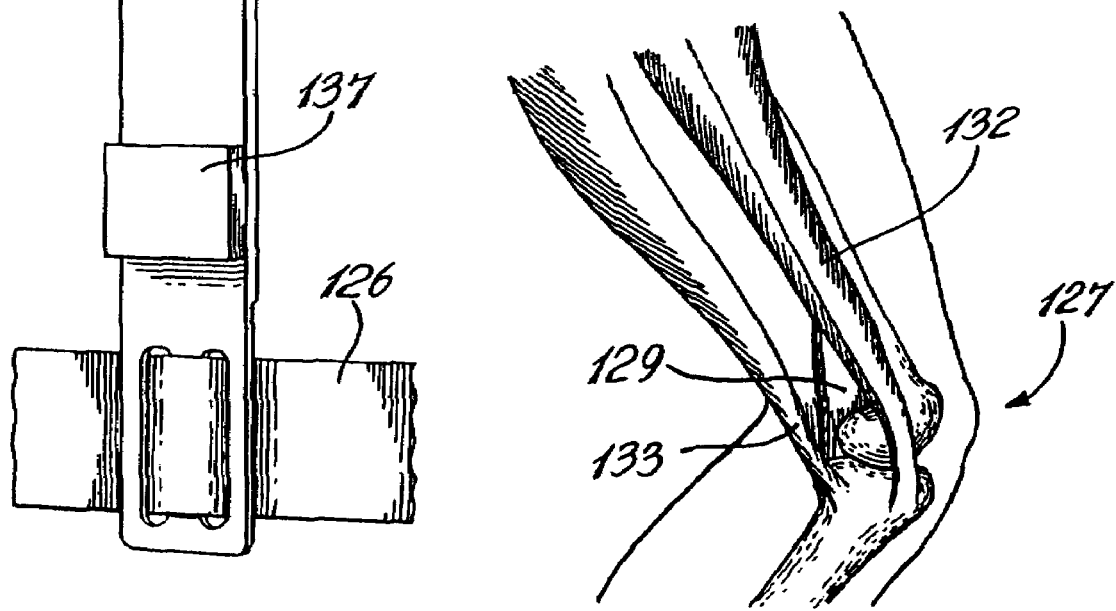
Fig. 3
Fig. 4a
Fig. 4b

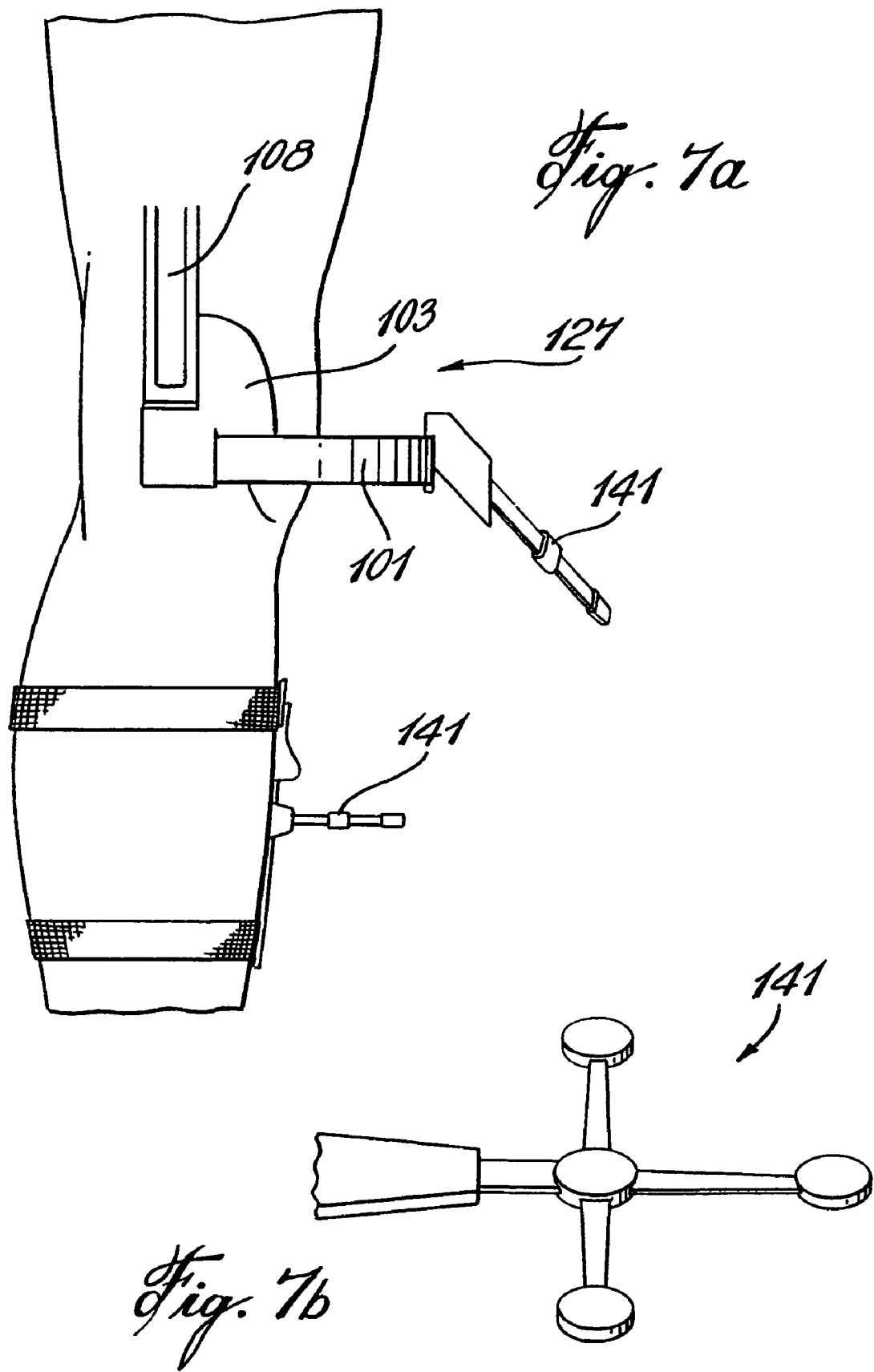

SYSTEM FOR THE ANALYSIS OF 3D KINEMATIC OF THE KNEE

FIELD OF THE INVENTION

The present invention relates to a knee harness and method for the precise and non-invasive measurement of knee motion and its analysis in 3D. Specifically, the present invention measures precisely and non-invasively the relative 3D position and orientation of the tibia in respect with the 3D position and orientation of the femur during time and the relative 3D movement of the tibia in respect of the femur.

BACKGROUND OF THE INVENTION

Human joints are usually more complex than a single axis. The knee joint is among the most complicated synovial joints in the musculoskeletal system. The kinematic studies of knee allow the computation of force distribution during physical activities (such as walking), evaluating surgical operations such as ligament reconstruction, evaluating the effects of inaccurate positioning of condylar prostheses, evaluating the effect on the knee of the use of foot prosthesis, evaluating diagnostic methods for ligament injuries and studying the injury mechanism in a knee joint.

By performing a combination of rolling and sliding, the knee joint accommodates the small contact area between the femur and the tibia. The anatomical structure of the femoral condyles leads to a complex combination of translations and rotations, which includes components of abduction/adduction, internal/external rotations and flexion/extension.

Some tools are known that allow an evaluation of the knee. Instrumented clinical tests as KT1000 [Bach et al., 1990] have been proposed, but their use is still under debate and their reliability and inter-observer reproducibility are questioned [Forster et al., 1989; Huber et al., 1997]. The Lars Rotational Laxiometer [Beacon et al., 1996; Bleday et al., 1998] seems to demonstrate a satisfactory inter and intra-observer reproducibility, but the measurement is limited to the laxity of the knee along one movement axis. Also, considering the 3D nature of the knee's movement, it is essential to complete this measurement by a more global evaluation, in 3D and in movement.

To measure the rotations, localising sensors (magnetic, optic, ultrasonic . . . ) can be used in order to follow the position and orientation of the femur and the tibia in space. Experiments have been made in order to measure the relative motion between the femur and the tibia using such sensors placed on the skin. However, Macleod and Morris (1987) were the first to study the inevitable relative movement between skin and bone during a movement analysis. This has also been done by Sati et al. (1996) who has reported three general methods which address the problem of relative skin movement: 1) use of intracortical pins to fix rigidly but invasively the sensors to the bones, 2) use of statistical calculations to correct the positions of several sensors and 3) use of attachment systems in order to reduce sensors movement in respect with the underlying bone. Only the third method allows having relatively precise measurements of the bone position and orientation, non-invasively. Because these two factors are essential during routine examinations of the knee, the use of an external attachment system seems to be the best compromise.

Sati et al. (1996) proposed an attachment system for the sensors. This mechanical fixation system attaches the sensors onto the underlying bone non-invasively. Three attachment sites onto the condyles are related with a mechanical bridge, which insure the application of inward clamping pressure. A vertical bar insures the system to accurately reflect the orientation of the femoral long axis. The tibial attachment consists of a long bow-shaped plate strapped at both ends to the proximal and distal ends of the tibia. It has been shown that the system can measure knee kinematics with acceptable precision (Sati et al. 1996). This attachment system however revealed some problems in its use:

The mechanical bridge which relates the attachment sites on the femoral harness is designed to be flexible in order to provide comfort to the subject when performing extension of the knee since biceps femoris tendon and ilio-tibial band approach one another during full extension, and the lateral attachment sits on the biceps femoris muscle which has the effect of pushing the lateral attachment away from the knee (Sati, 1996). However, this causes a displacement of the three femoral attachments, particularly on the lateral side, that produces an antero-posterior force which can lead to harness detachment. Also, the localising sensors motion is then influenced by their location on the attachment system.

Moreover, the mechanical bridge flexibility causes orientation changes in part of the harness during subject full extension, which can result in errors in measurements of the position and orientation of the sensors fixed on the harness. Further, the addition of force exerted on knee structures when performing full extension is similar for all subjects. Although it can be acceptable for many subjects, the force can be unbearable for some. Finally, the adjustment and installation is somewhat long and not precise.

A second version of the harness was produced, with a bridge that is rigid in expansion but flexible in torsion, relating one lateral and two medial supports. No lateral expansion is possible during knee extension because of the bridge's rigidity in expansion, which produces an unbearable pressure on both sides of the knee for most of the subjects and causes errors in measurements.

Due to these disadvantages, there is a need to provide a new harness design in order to improve the precision, the sensibility and the reproducibility of the knee analysis system without affecting the subject's comfort.

SUMMARY OF THE INVENTION

It is therefore a feature of the present invention to overcome the disadvantages of the prior art and provide a harness and method of use which permits precise measurements and analysis of the knee movement, i.e. the description during time of the tibial and femoral three-dimensional positions and orientations, one with respect to the other.

It is a further feature of the present invention to provide a harness which can obtain a non-invasive attachment for the localising sensors on the femur, which is composed of orthoplasts, not related by a flexible mechanical bridge, and which is comfortable for the subject, especially during full extension.

It is a still further feature of the present invention to provide an attachment system that can be installed on a subject's knee rapidly and precisely.

In accordance with the above features, from a broad aspect, the present invention provides a knee movement analysis system composed of a rigid harness which fixates, in a non-invasive manner, localising sensors on the femur, and an attachment system which fixates, in a non-invasive manner, localising sensors onto the tibia, and a program analysing the location measurements, therewith providing results on kinematic or posture of the knee.

The present invention differs from the prior art in that it consists of a three-dimensional knee movement analysis system, which uses a rigid attachment system for localising sensors on the femur and on the tibia. The rigidity of the femoral harness is compensated by a new design of the two orthoplasts, which absorb by mean of springs, the lateral pressure forces due to knee expansion when performing a full range of motion.

The harness rigidity provides improvements in sensors stability and precision in respect with the femur, in rapidity of installation on the knee and in comfort for the subject and thus, improvements in the precision, the quality, and the reproducibility of knee evaluation.

According to a further broad aspect of the present invention there is provided a harness for attachment about a knee femur of the subject. The harness comprises a rigid and non-flexible frame supporting two resiliently mounted clamping means. The clamping means are urged under pressure outwardly for application against a skin outer surface at predetermined medial and lateral sites relative to a femur. A non-resilient adjustable stabilising element is connected to the rigid frame and disposed at a predetermined location with respect to the medial clamping means in spaced relationship therewith and adjustable for clamping contact on a skin outer surface and in alignment with the centre of a medial condyle of the femur whereby to stabilise the rigid frame about a knee. An attachment means is secured to the harness and has means for securement above the knee.

According to a further broad aspect of the present invention the harness attaches about the knee femur of a subject in a non-invasive system for precise and reproducible three-dimensional movement analysis of the knee. The system also comprises attachment means associated to a knee tibia in a fixed relationship. Localising sensors are secured to the harness and to the tibial attachment means. The sensors provide position and orientation indications associated with the femur and the tibia in space. A means is also provided to generate data corresponding to the position and orientation of the sensors, in time.

According to a further still broad aspect of the present invention there is provided a method of determining the kinematic of a knee in a non-invasive manner. The method comprises the harness as above described attached about the knee femur and the tibial attachment means is secured to the knee tibia in a fixed relationship. Data is generated by localising sensors secured to the harness and the tibial attachment means. The data localises the sensors in space and in time. The location of the sensors is detected at specific time intervals to provide location data at the time intervals. The data is treated, analysed and resulting data is generated for use in the description of a knee to which the harness and tibial attachment means is secured.

The above described method is further characterised in that the resulting data consists of steps of defining a coordinate system relative to the group of sensors fixed to the harness, defining a coordinate system relative to the group of sensors fixed on the tibial attachment means and calculating the mathematical relationship between the coordinate systems one to another.

BRIEF DESCRIPTION OF DRAWINGS

FIG. 3 is a perspective view of tibial attachment means;

FIGS. 4a and 4b are respectively medial and lateral views of the anatomical structures of the knee, permitting the identification of installation sites of the harness on the knee;

FIG. 7a is a fragmented side view of a leg showing the harness and tibia attachment bar secured thereto with ultrasound localising sensors; and FIG. 7b is a perspective view of an ultrasound localising sensor.

DESCRIPTION OF THE PREFERRED EMBODIMENTS

Figure 1:
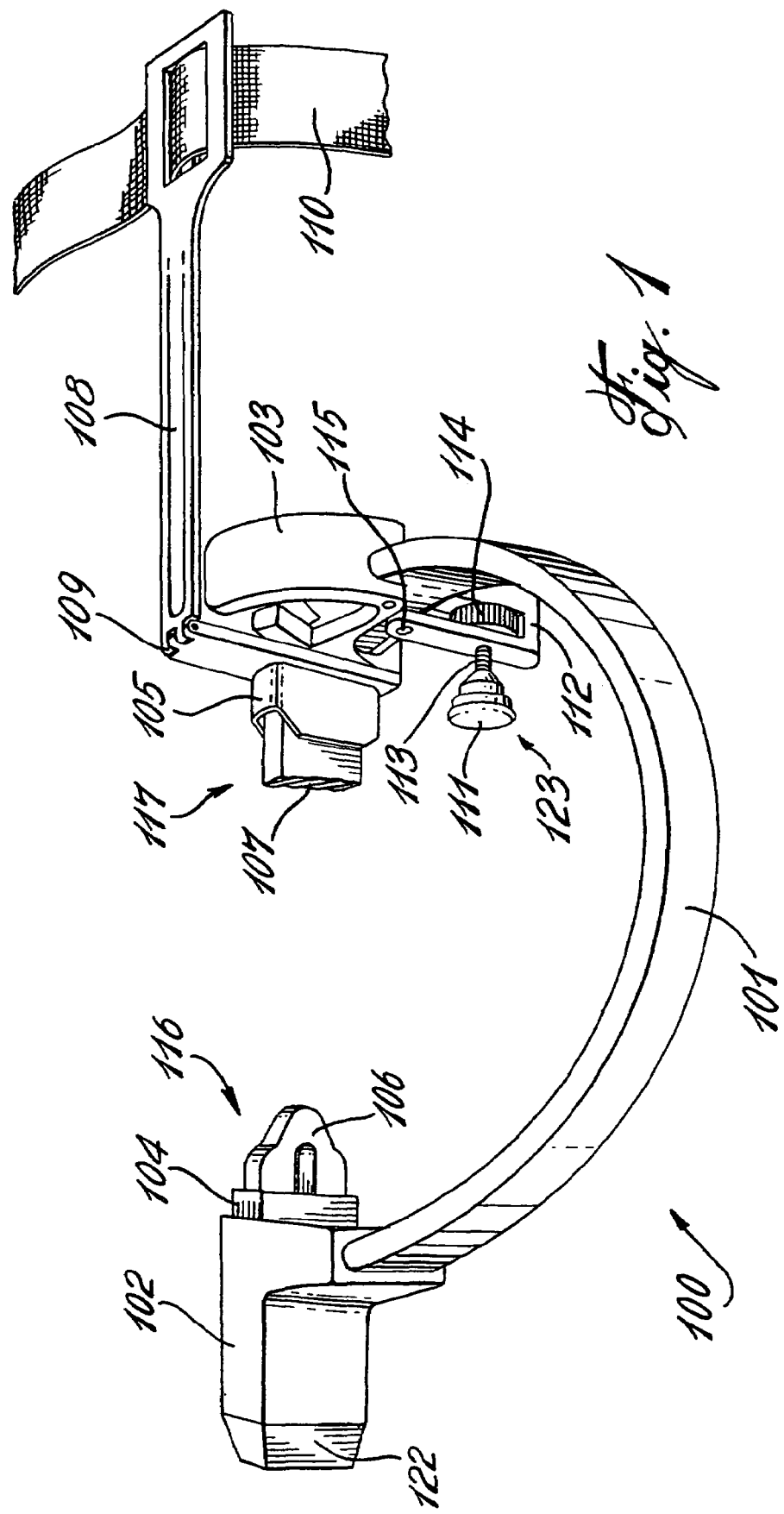
FIG. 1 is a perspective view of the harness constructed in accordance with the present invention.
Figure 2:
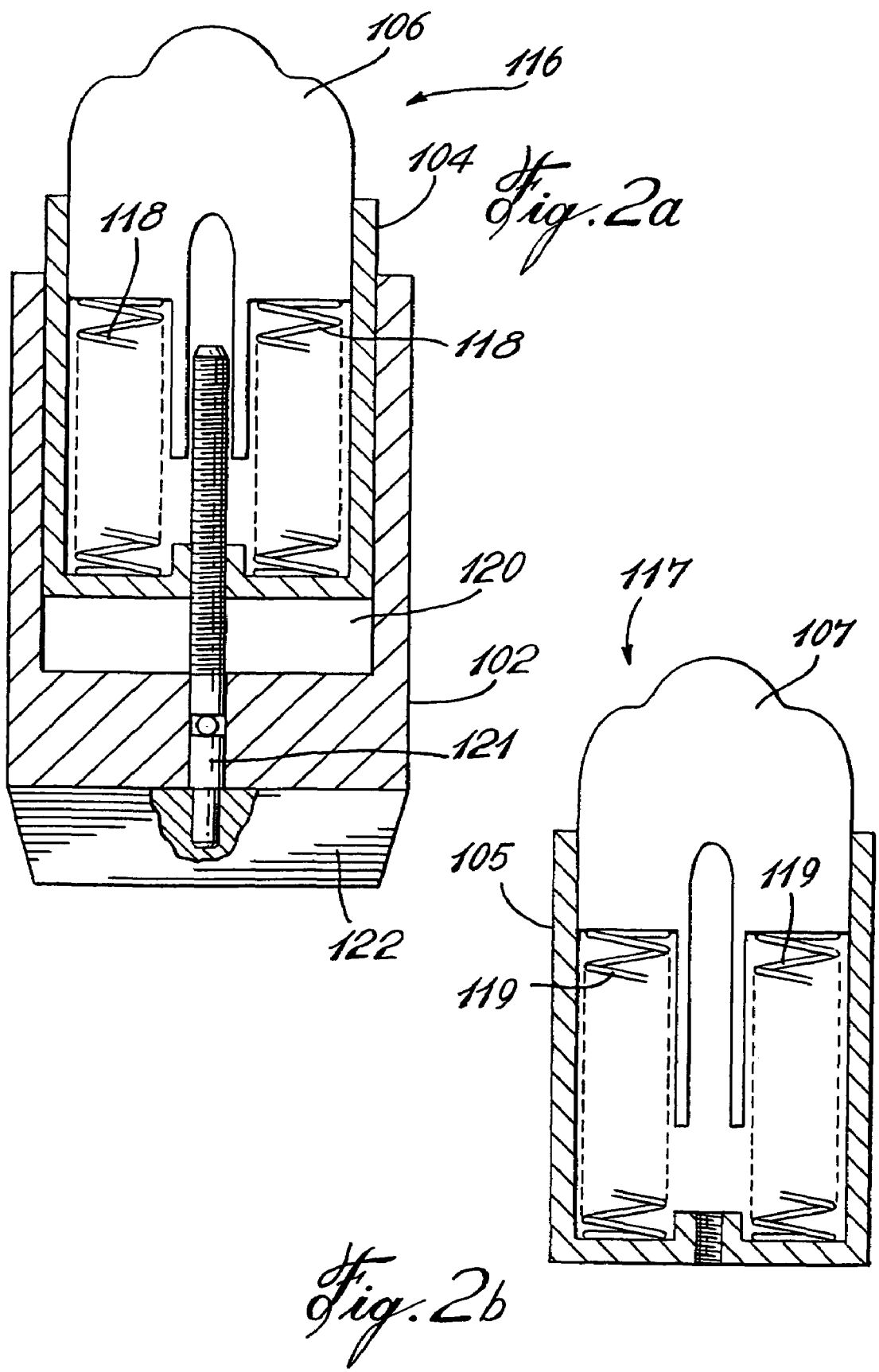
FIGS. 2a and 2b are sectional views of the clamping means located on the lateral and medial side of the knee, respectively.
Figure 5:
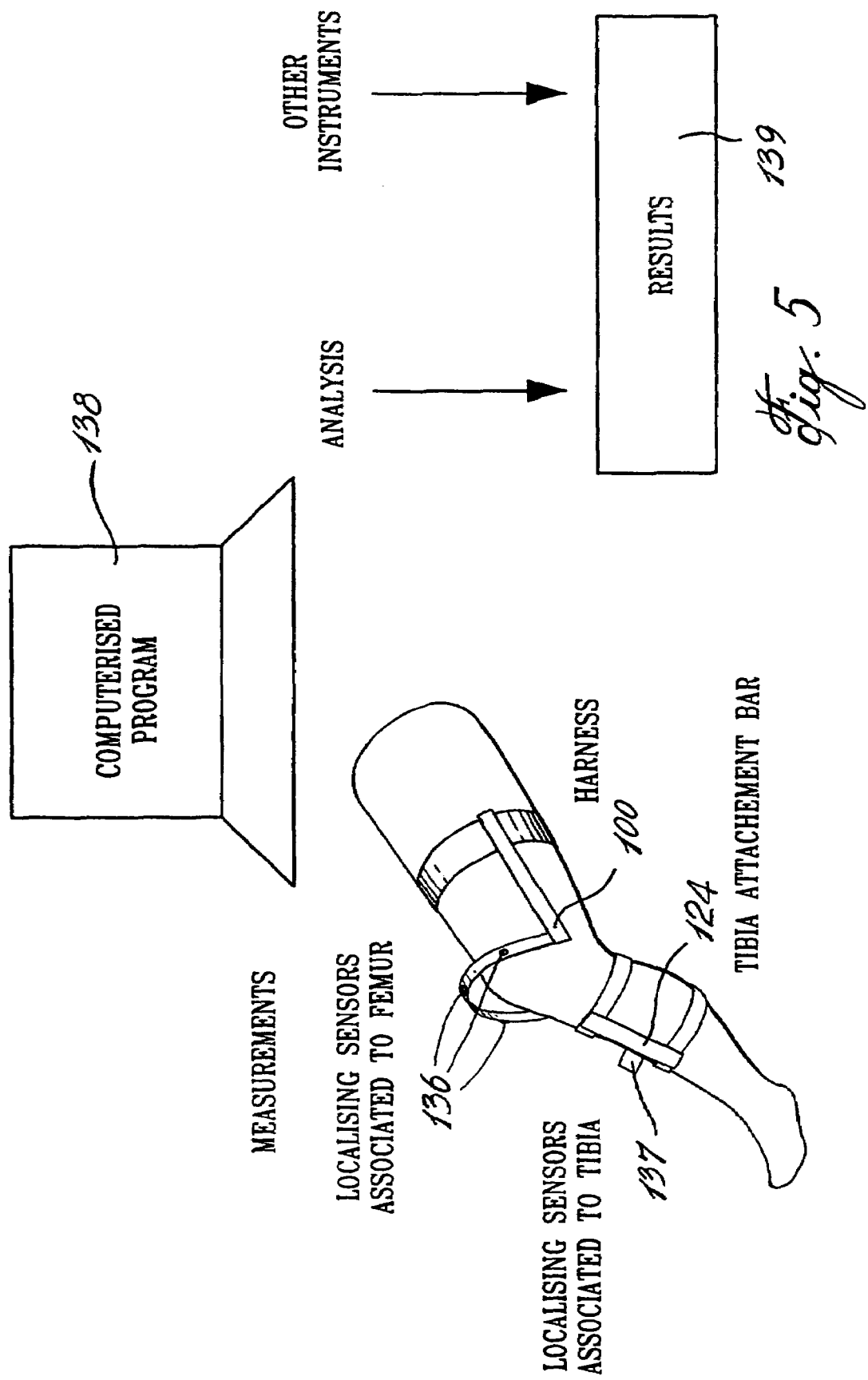
FIG. 5 is a schematic and block diagram representing the system for analysis of the three-dimensional kinematic of the knee.

Referring to FIGS. 1 and 2, the harness 100 of the present invention is described. This harness 100 comprises a rigid and non-flexible frame 101 which is formed as a rigid arch. At each end of the frame there is provided a medial rigid support 103 and a lateral rigid support 102. The distance between the ends is fixed or adjustable.

The harness 100 further comprises two resilient clamping means, 116 and 117 as shown in FIGS. 2a and 2b, each of them comprising a rigid housing 104 and 105 in which there is retained two rigid abutment elements 106 and 107 each having an outer end configured to fit the shape of a condyle. Springs 118 and 119, or any other resilient means, apply an outward force on the abutment elements. At least one of the clamping means 116 or 117 could be secured to rigid supports 102 or 103 by adjustable means, e.g. in sliding fit adjustment in a cavity 120 formed in rigid support 102. This adjustable means is hereinshown as being an adjustment screw 121 having a finger gripping head 122. The springs 118 and 119 are also interchangeable to vary the force of the abutment elements 106 and 107.

The harness 100 further comprises a non-resilient adjustable stabilising element 123 comprising a threaded rod 113 having an abutment pad 111 at an outer end thereof. This stabilising element 123 is being secured to a support frame 112, which support frame 112 is connected to the rigid frame 103 by adjustable means herein a screw attachment 115. The position of the pad 111 is adjusted by an adjustment wheel 114.

The harness 100 further comprises an attachment means in the form of a bar 108. This attachment bar 108 is in the form of a long narrow flat plate and could be formed of two sections interconnected by a hinge 109 or by a pivot. The attachment bar 108 could be secured by a Velcro™ strap 110 or by other attachment means above the knee of the wearer.

Referring now to FIG. 3, the tibial attachment means is described. This attachment means comprises a tibia attachment bar 124 secured below the knee by means of two adjustable Velcro straps 125 and 126, or by other attachment means. This attachment bar 124 is also in the form of a long narrow flat plate.

Referring to FIGS. 1, 4a and 4b, the installation of the harness 100 on knee 127 is described. The harness 100 is installed on the knee 127 by urging the abutment elements 105 and 107 of the clamping means 116 and 117 against the skin at predetermined sites 128 and 129 on the knee. These predetermined sites are located medially between the vastus medialis 130 and the sartorius tendon 131 of the knee and laterally between the ilio-tibial band 132 and the biceps femoris tendon 133 of the knee. The harness 100 is thereafter secured proximally, rigidly attaching the attachment bar 108 against the medial side of the thigh and securing this attachment bar by means of the Velcro™ strap 110. Without affecting subject's comfort, the harness stability is adjusted by means of the adjustable screw wheel 114 as well as the adjustment of the abutment element 106 by rotating the head 122. The abutment pad 111 of the stabilising element 123 is urged against skin in alignment with the centre of the medial condyle 128.

Referring to FIGS. 3, 4a and 4b, the installation of the tibial attachment on the knee 127 is described. The tibia attachment bar 124 is installed by adjusting its position so that the bar 124 urges on the anterior side of the tibia, below the tuberosity 134 of the tibia 135, securing the tibia attachment bar 124 below this tuberosity by means of the adjustable straps 125 and 126.

Figure 6A:
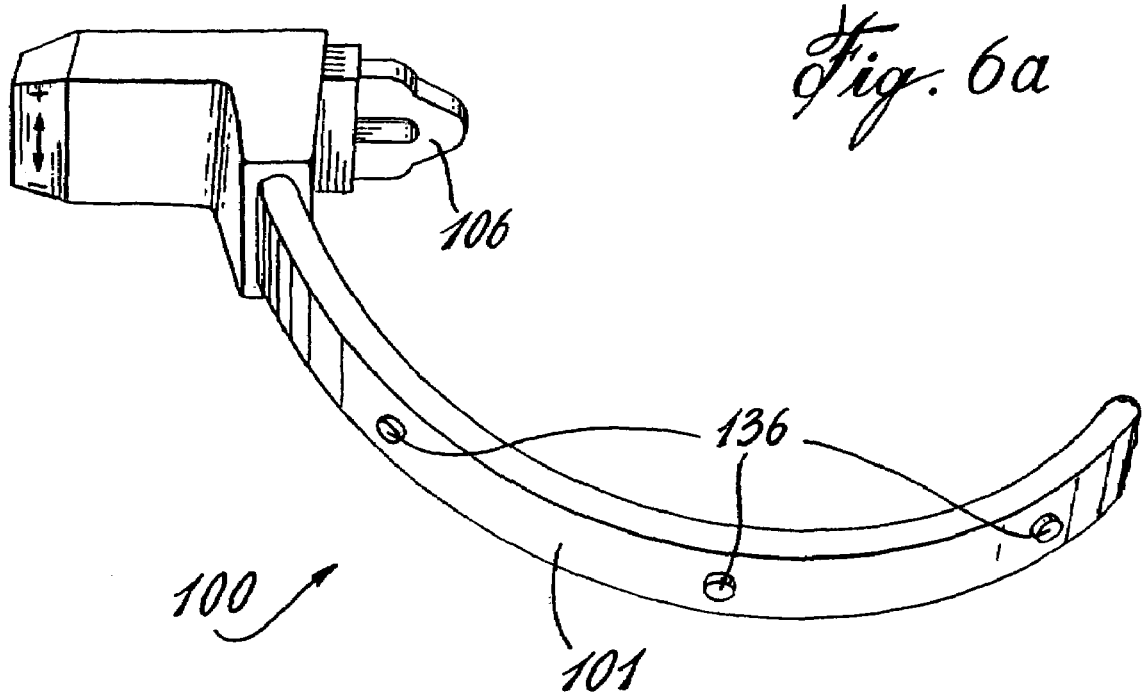
FIGS. 6a and 6b are perspective views, of the localising sensor secured against the harness, respectively, for contact with the anterior and lateral side of the knee.
Figure 6B:
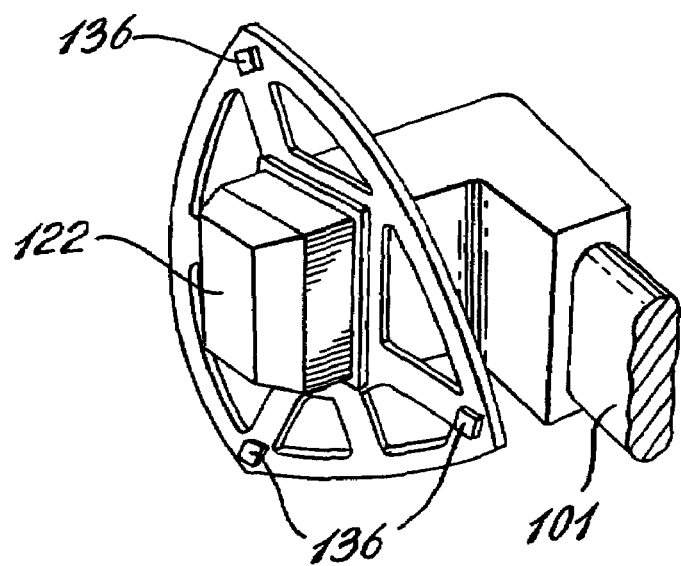

Referring to FIGS. 5, 6, 7a and 7b, the method for analysing the three-dimensional kinematic of a knee will be described. A harness 100 and the tibial attachment bar 124 are provided with localising sensors 136, 137 or 141 on the femur of the knee and on the tibia. The localising sensors are designated by reference numeral 136, 137 and 141 and can be of different types, herein illustrated are electromagnetic sensors 137, opto-electronic sensors 136, and ultrasonic sensors 141. These sensors are incorporated in a system to provide data on their three-dimensional positions or their three-dimensional positions and orientations, with respect to an external reference, or with respect to one another. FIG. 6 illustrates an example of the position of opto-electronic sensors 136 on the harness 100. Their positions are tracked using a camera (not shown). When using the ultrasonic sensors 141, their positions are tracked by ultrasound tx/rx methods. Their three-dimensional position and orientation can also be determined by their relationship to one another. When using electromagnetic tracking sensors 137 their three-dimensional position and orientation is tracked with electromagnetic field emitter/receiver methods.

The harness 100 and the tibial attachment bar 124 are installed on the knee to be analysed. A knee posture is adopted or movement of the knee is performed. This movement could consist of walking, or walking on a treadmill, or bending and/or stretching the knee . . . The movement could be guided by a person or by an apparatus. Data is generated by the localising sensors 136, 137, and 141 and the data is treated and analysed by computerised program means 138 or equivalent electronic means. The treatment of the data could reside in the calculation of mathematical relationships relating the femur with the tibia in space during time. These relationships could be calculated with the definition on the femur and on the tibia of a coordinate system representing the location of the femur and the tibia, respectively. This latter definition could be accomplished on computerised models which are thereafter calibrated on real bones.

The mathematical relationships, rotations, translations, helicoïdal axis, . . . etc are used to calculate knee movement indexes data 139 used in the description of the posture, or the movement of the knee.

Briefly summarising the method of determining the kinematic of a knee in a non-invasive manner comprising the harness of the present invention, the method comprises attaching the harness about a knee femur in the manner as above described and securing the tibial attachment bar to the knee tibia in a fixed relationship. Data is generated by the localising sensors secured to the harness and the tibial attachment bar. This data localises the sensors in space and in time. The location of the sensors is detected at specific time intervals to provide location data at the time intervals. This data is treated, analysed and resulting data is generated which describes the knee to which the harness and tibial attachment means is secured.

In installing the harness about the knee care is taken to place one of the clamping means between the vastus medialis and the sartorius tendon of the knee. The other clamping means is positioned between the ilio-tibial band and the biceps femoris tendon of the knee. The attachment rod which is connected to the harness is placed against the medial side of thigh and attached by means of straps above the knee. The stability of the harness is verified even after the knee has been flexed a few times. The position of the stabilising element on the medial side is adjusted so that one extremity urges against the skin in alignment with the centre of the condyle when the knee is in extension. The position of the attachment means is adjusted so that it urges on the interior side of the tibia below the two tuberosity of the tibia and it is attached below the two tuberosity of the tibia.

The measurements are taken when the knee is in movement and this is achieved by walking on a floor surface or walking on a treadmill or jumping at least one or a few times, or bending the knee at least once or stretching the knee at least one time. The movement is guided by a person or an apparatus.

The analysis of data consists of defining a coordinate system relative to the group of sensors fixed to the harness, and defining a coordinate system relative to the group of sensors fixed on the tibial attachment rod. The mathematical relationship between the coordinate systems one to another is then calculated. The measurement is effected by a computerised three-dimensional representations of the femur and tibia and these representations are calibrated in order to be accurately positioned and oriented relative to real femur and tibia bones. The mathematical relationship is defined by rotations and translations to the femur and tibia with respect to one another as well as a finite helicoïdal axis of the knee. The resulting data represents Euler angles and distances described at predetermined time intervals. The resulting data not only represents three-dimensional orientations and positions of finite helicoïdal axis of the knee but also angle of rotation around the helicoïdal axis and translation along the helicoïdal axis described at predetermined time intervals.

The tibial attachment bar 124 is composed of a rigid rod approximately 3 cm wide, 25 cm long and 3 mm thick.

It is within the ambit of the present invention to cover any obvious modifications of the preferred embodiment described herein, provided such modifications fall within the scope of the appended claims.

We claim:

1. A harness for attachment about a knee femur of a subject, said harness comprised of a rigid and non-flexible frame adapted to be supported spaced apart from the knee and without contacting the leg by two resiliently mounted clamping means and a non-resilient adjustable stabilising element so as not to limit motion of the knee, said clamping means being urged under pressure outwardly for application against a skin outer surface at predetermined medial and lateral sites relative to a femur, the non-resilient adjustable stabilising element connected to said rigid frame and disposed at a predetermined location with respect to said medial clamping means in spaced relationship therewith and adjustable for clamping contact on a skin outer surface and in alignment with a medial condyle of the femur whereby to stabilise said rigid frame about a knee, said stabilising element comprising a rod having an abutment pad at an outer end thereof, said pad being positioned for contact on the centre of the medial femoral condyle, and an attachment means secured to said harness and having means for securement above the knee.

2. A harness as claimed in claim 1 wherein one of said clamping means is secured to said rigid frame in fixed relationship.

3. A harness as claimed in claim 1 wherein at least one of said clamping means are secured to said rigid frame in an adjustable relationship.

4. A harness as claimed in claim 1 wherein said clamping means are spaced apart at outer ends thereof a predetermined distance for abutment on opposed sides of a knee in a medio-lateral direction.

5. A harness as claimed in claim 1 wherein the said stabilising element is adjustably secured to a support frame, said support frame being adjustably connected to said rigid non-flexible frame.

6. A harness as claimed in claim 1 wherein said attachment mean is comprised by a bar connected to said frame, said bar being formed by two bar sections interconnected by a hinge, said bar being positioned for skin surface contact against medial portion of the thigh, said mean for securement being an adjustable strap.

7. A harness as claimed in claim 1 wherein said attachment means is comprised by a bar connected to said frame, said bar being formed by two bar sections interconnected by a pivot, said bar being positioned for skin surface contact against medial portion of the thigh, said means for securement being an adjustable strap.

8. A harness as claimed in claim 1 wherein said attachment means is comprised by a bar connected to said frame, said bar being positioned for skin surface contact against medial portion of the thigh, said means for securement being an adjustable strap.

9. A harness as claimed in claim 1 wherein said rigid and non-flexible frame is composed of a rigid arch with a medial extremity adapted to be located on a medial side of the knee and a lateral extremity adapted to be located on a lateral side of the knee, said clamping means, said stabilising element and said attachment means being secured to said arch.

10. A harness as claimed in claim 1 wherein said rigid and non-flexible frame is composed of a rigid arch, said arch having one medial extremity adapted to be located on a medial side of the knee, said medial extremity being secured to a medial rigid frame adapted to be located on a medial side of the knee, said arch having a lateral extremity adapted to be located on a lateral side of the knee, said lateral extremity being secured to a lateral rigid frame adapted to be located on said lateral side of the knee, said harness having one of said clamping means being secured to said lateral rigid frame; said harness having one of said clamping means, said stabilising element and said attachment means being secured to said medial rigid frame.

11. A harness as claimed in claim 1 wherein said rigid and non-flexible frame comprises a medial extremity adapted to be located on a medial side of the knee and a lateral extremity adapted to be located on lateral side of the knee, said lateral and medial extremities being related in an adjustable relationship; said clamping means, said stabilising element and said attachment means being secured to said non-flexible frame.

12. A harness as claimed in claim 1 wherein said predetermined medial site for one of said clamping means is between the vastus medialis and the sartorius tendon.

13. A harness as claimed in claim 1 wherein said predetermined lateral site for one of said clamping means is between the ilio-tibial band and the biceps femoris tendon.

14. A harness as claimed in claim 1 wherein said two resilient clamping means each comprises a rigid housing in which there is displaceably retained a rigid abutment element which has an outer end configured to fit the shape of the condyle, said rigid abutment element having an inner portion retained by said housing in guided relationship and urged outwardly by resilient means captive in said housing.

15. A harness as claimed in claim 14 wherein said resilient means is constituted by at least one interchangeable spring.

16. A harness as claimed in claim 14 wherein at least one said housing is secured in sliding fit displacement in a cavity formed in said rigid frame, said displacement permitting to position said housing at a desired position within said cavity.

17. A harness as claimed in claim 16 wherein said sliding fit displacement is produced by means of an adjustment screw.

18. A system for the precise and reproducible three-dimensional movement analysis of a knee, said system comprising:
a harness adapted to be supported about a knee femur of a subject, said harness comprised of a rigid and non-flexible frame supported spaced apart from the knee by two resiliently mounted clamping means so as not to limit motion of the knee, said clamping means being urged under pressure outwardly for application against a skin outer surface at predetermined medial and lateral sites relative to a femur, the non-resilient adjustable stabilising element connected to said rigid frame and disposed at a predetermined location with respect to said medial clamping means in spaced relationship therewith and adjustable for clamping contact on a skin outer surface and in alignment with a medial condyle of the femur whereby to stabilise said rigid frame about a knee, and an attachment means secured to said harness and having means for securement above the knee;
tibial attachment means associated to a knee tibia in a fixed relationship, the tibial attachment means not being connected to the harness,
localising sensors secured to said harness and to said tibial attachment means, said sensors providing position and orientation indications associated with the femur and the tibia, in space,
means to generate data corresponding to said position and orientation of said sensors, in time.

19. The system as claimed in claim 18 further comprising means for treating said data, to calculate knee movement indexes and providing resulting data in storage form for use in the analysis of the kinematics of a knee.

20. The system as claimed in claim 18 further comprising means for treating said data, to calculate knee posture indexes and providing resulting data in storage form for use in the analysis of the posture of a knee.

21. The system as claimed in claim 18 wherein said tibial attachment means comprises a rod, said rod being connectable on a skin outer surface, said skin outer surface being located on an anterior side of the tibia and below the tibial tuberosity, said rod being secured proximally and distally by adjustable straps for securement about the lower leg portion below the knee.

22. The system as claimed in claim 18 wherein said tibial attachment means is composed of a rigid rod approximately 3 cm wide, 25 cm long and 3 mm thick.

23. The system as claimed in claim 18 wherein said localising sensors are electromagnetic tracking devices which locate their three-dimensional position and orientation in respect to an electromagnetic field emitter.

24. The system as claimed in claim 18 wherein said localising sensors are opto-electronic tracking devices which emit optical signal which are received by a camera, said camera enabled to follow the three-dimensional position of each sensor.

25. The system as claimed in claim 18 wherein said localising sensors are ultrasonic tracking devices which locate their three-dimensional position and orientation in respect to an ultrasound emitter.

26. The system as claimed in claim 18 wherein said localising sensors are ultrasonic tracking devices which locate their three-dimensional position and orientation with respect to one another.

27. A method of determining the kinematics of a knee in a non invasive manner comprising the steps of:
   (i) providing a harness for attachment about a knee femur of a subject, said harness comprised of a rigid and non-flexible frame adapted to be supported spaced apart from a knee by two resiliently mounted clamping means and a non-resilient adjustable stabilising element so as not to limit motion of the knee, said clamping means being urged under pressure outwardly for application against a skin outer surface at predetermined medial and lateral sites relative to a femur, the non-resilient adjustable stabilising element connected to said rigid frame and disposed at a predetermined location with respect to said medial clamping means in spaced relationship therewith and adjustable for clamping contact on a skin outer surface and in alignment with a medial condyle of the femur whereby to stabilise said rigid frame about a knee, and an attachment means secured to said harness and having means for securement above the knee,
   (ii) installing said harness about a knee to be analysed,
   (iii) securing tibial attachment means to the knee tibia in a fixed relationship and separated from the harness,
   (iv) generating data by localising sensors secured to said harness and said tibial attachment means, said data localising said sensors in space and in time,
   (v) detecting the location of said sensors at specific time intervals to provide location data at said time intervals,
   (vi) treating and analysing said data, and
   (vii) generating resulting data for use in the description of a knee to which said harness and tibial attachment means is secured.

28. A method as claimed in claim 27 wherein said step (ii) of installing said harness about a knee comprises the steps of:
   (i) placing one of said clamping means between the vastus medialis and the sartorius tendon of said knee,
   (ii) placing one of said clamping means between the ilio-tibial band and the biceps femoris tendon of said knee,
   (iii) placing said attachment means against the medial side of the thigh,
   (iv) securing the attachment means above said knee,
   (v) verifying that said harness is stable about said knee, even after a few movements of flexion-extension of said knee,
   (vi) adjusting the position of said stabilising element on a medial side, so that one extremity urges against the skin in alignment with the centre of the condyle when said knee is in extension.

29. A method as claimed in claim 27 wherein the step (iii) installation of said tibial attachment means on said tibia at said predetermined site comprises the steps of:
   (i) adjusting the position of said tibial attachment means so that it urges on the anterior side of said tibia, below the tuberosity of said tibia, and
   (ii) securing said tibial attachment means below said tuberosity of said tibia.

30. A method as claimed in claim 27 wherein there is provided the step of measuring at predetermined time intervals the three-dimensional positions of a group of at least three sensors fixed on said harness and of a group of at least three sensors fixed on said tibial attachment means, said positions being measured with respect of an external reference; and the further step of calculating the three-dimensional positions and orientations of each said group of sensors with respect to said external reference, said sensors generating data on their three-dimensional positions relatively to said external reference.

31. A method as claimed in claim 27 wherein there is provided the step of measuring at predetermined time intervals the three-dimensional position and orientation of at least one sensor on said harness and at least one sensor on said tibial attachment means, said position and orientation being measured with respect to an external reference, said sensors generating data on their three-dimensional position and orientation relative to said external reference.

32. A method as claimed in claim 27 wherein there is provided the step of measuring at predetermined time intervals the three-dimensional position and orientation of a group of at least three sensors fixed on said harness with respect to a group of at least three sensors fixed on said tibial attachment means; and the further step of calculating the three dimensional position and orientation of said group of sensors fixed on said harness in respect to said group of sensors fixed on said tibial attachment means, said sensors fixed on said harness generating data on their three-dimensional positions relative to said group of sensors fixed on said tibial attachment means.

33. A method as claimed in claim 27 wherein there is provided the step of measuring at predetermined time intervals the three-dimensional positions and orientations of a group of at least three sensors fixed on said tibial attachment means with respect to a group of at least three sensors fixed on said harness; and the further step of calculating the three-dimensional position and orientation of said group of sensors fixed on said tibial attachment means with respect to said group of sensors fixed on said harness, said sensors fixed on said tibial attachment means generating data on their three-dimensional position relative to said group of sensors fixed on said harness.

34. A method as claimed in claim 27 wherein there is further provided the step of measuring at predetermined time intervals the three-dimensional position and orientation of at least one sensor fixed on said tibial attachment means with respect to at least one sensor fixed on said harness, said sensor fixed on said tibial attachment means generating data on its three-dimensional position and orientation with respect to said at least one sensor fixed on said harness.

35. A method as claimed in claim 27 wherein there is provided the step of measuring at predetermined time intervals the three-dimensional position and orientation of at least one sensor fixed on said harness with respect to at least one sensor fixed on said tibial attachment means, said sensor fixed on said harness generating data on its three-dimensional position and orientation with respect to said sensor fixed on said tibial attachment means.

36. A method as claimed in claim 27 wherein said analysis of data is performed by computerised program means.

37. A method as claimed in claim 27 wherein said analysis of data is performed by electronic means.

38. A method as claimed in claim 27 which further comprises the step of causing movement of said knee.

39. A method as claimed in claim 38 wherein said movement is walking.

40. A method as claimed in claim 38 wherein said movement is walking on a treadmill.

41. A method as claimed in claim 38 wherein said movement is jumping at least one time.

42. A method as claimed in claim 38 wherein said movement is bending said knee at least one time.

43. A method as claimed in claim 38 wherein said movement is stretching said knee at least one time.

44. A method as claimed in claim 38 wherein said movement is guided by a person.

45. A method as claimed in claim 38 wherein said movement is guided by an apparatus.

46. A method as claimed in claim 27 wherein said analysis of data consists of:
 (i) defining a coordinate system relative to said group of sensors fixed to said harness,
 (ii) defining a coordinate system relative to said group of sensors fixed on said tibial attachment means, and
 (iii) calculating the mathematical relationship between said coordinate systems one to another.

47. A method as claimed in claim 46 wherein said coordinate systems are measured by means of computerised three dimensional representations of said femur and tibia, said representations being calibrated in order to be accurately positioned and orientated relative to real femur and tibia bones.

48. A method as claimed in claim 46 wherein said mathematical relationship is defined by rotations and translations of said femur and tibia with respect to one another.

49. A method as claimed in claim 46 wherein said mathematical relationship is defined by a finite helicoidal axis of said knee.

50. A method as claimed in claim 46 wherein said resulting data represent Euler angles and distances described at predetermined time intervals.

51. A method as claimed in claim 46 wherein said resulting data represent three-dimensional orientations and positions of finite helicoidal axis of said knee, angle of rotation around said helicoidal axis and translation along said helicoidal axis, described at predetermined time intervals.

52. A harness for attachment about a knee femur of a subject, said harness comprised of a rigid and non-flexible frame adapted to be supported spaced apart from the knee and without contacting the leg by two resiliently mounted clamping means and a non-resilient adjustable stabilising element so as not to limit motion of the knee, said two resilient clamping means each comprising a rigid housing in which there is displaceably retained a rigid abutment element which has an outer end configured to fit the shape of the condyle, said rigid abutment element having an inner portion retained by said housing in guided relationship and urged outwardly by resilient means captive in said housing, with at least one said housing being secured in sliding fit displacement in a cavity formed in said rigid frame, said displacement permitting to position said housing at a desired position within said cavity, whereby said clamping means is urged under pressure outwardly for application against a skin outer surface at predetermined medial and lateral sites relative to a femur, the non-resilient adjustable stabilising element connected to said rigid frame and disposed at a predetermined location with respect to said medial clamping means in spaced relationship therewith and adjustable for clamping contact on a skin outer surface and in alignment with a medial condyle of the femur whereby to stabilise said rigid frame about a knee, and an attachment means secured to said harness and having means for securement above the knee.

* * * * *